(12) United States Patent
Dey et al.

(10) Patent No.: US 10,889,717 B2
(45) Date of Patent: *Jan. 12, 2021

(54) COMPOSITIONS, METHODS, AND TEST KITS FOR DETERMINING AUTHENTICITY

(71) Applicant: Milliken & Company, Spartanburg, SC (US)

(72) Inventors: Sanjeev K. Dey, Spartanburg, SC (US); Haihu Qin, Greer, SC (US); Gregory S. Miracle, Liberty Township, OH (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/157,895

(22) Filed: Oct. 11, 2018

(65) Prior Publication Data

US 2019/0112484 A1  Apr. 18, 2019

Related U.S. Application Data

(60) Provisional application No. 62/571,757, filed on Oct. 12, 2017, provisional application No. 62/596,401, filed on Dec. 8, 2017.

(51) Int. Cl.
| | | |
|---|---|---|
| *C09B 11/26* | (2006.01) | |
| *A61K 8/49* | (2006.01) | |
| *C09B 11/12* | (2006.01) | |
| *A61Q 13/00* | (2006.01) | |
| *C11D 3/40* | (2006.01) | |
| *A61K 8/41* | (2006.01) | |
| *C11D 3/50* | (2006.01) | |
| *G01N 21/78* | (2006.01) | |

(52) U.S. Cl.
CPC .............. *C09B 11/26* (2013.01); *A61K 8/411* (2013.01); *A61K 8/492* (2013.01); *A61K 8/4986* (2013.01); *A61Q 13/00* (2013.01); *C09B 11/12* (2013.01); *C11D 3/40* (2013.01); *C11D 3/50* (2013.01); *G01N 21/78* (2013.01)

(58) Field of Classification Search
CPC ........................................................ C09B 11/26
USPC .......................................................... 549/29
See application file for complete search history.

(56) References Cited

U.S. PATENT DOCUMENTS

| 2008/0196176 A1 | 8/2008 | Torres et al. |
| 2015/0322384 A1 | 11/2015 | Butterfield et al. |
| 2016/0326467 A1 | 11/2016 | Qin et al. |

FOREIGN PATENT DOCUMENTS

GB            1 047 796 A      11/1966

OTHER PUBLICATIONS

PCT/US2018/055446 International Search Report, filed Oct. 11, 2018, 7 pages.
PCT/US2018/055446 Written Opinion of The International Searching Authority, filed Oct. 11, 2018, 13 pages.

*Primary Examiner* — Taofiq A Solola
(74) *Attorney, Agent, or Firm* — Robert M. Lanning

(57) ABSTRACT

The present disclosure provides composition having at least one leuco composition conforming to Formula (I):

$$Ar^1Ar^2Ar^3CH \qquad (I)$$

wherein $Ar^2$ and $Ar^3$ are independently a carbocyclic aryl or heteroaryl, and $Ar^1$ is selected from the group consisting of: unsubstituted phenyl, electron deficient carbocyclic aryl, and heteroaryl. The present disclosure also provides a method of detecting an authentic composition and test kits for detecting authentic compositions.

12 Claims, No Drawings

COMPOSITIONS, METHODS, AND TEST KITS FOR DETERMINING AUTHENTICITY

CROSS REFERENCE TO RELATED APPLICATIONS

This application claims, pursuant to 35 U.S.C. § 119(e), priority to and the benefit of the filing date of U.S. Patent Application No. 62/571,757 filed on Oct. 12, 2017 and U.S. Patent Application No. 62/596,401 filed on Dec. 8, 2017, the contents of which are hereby incorporated by reference.

FIELD OF THE INVENTION

This application describes compositions comprising at least one leuco composition and the use of these compositions in distinguishing authentic from counterfeit goods. The leuco compositions are provided in a stable, colorless, or substantially colorless state and are incorporated into target compositions. This application further relates to methods for determining an authentic composition comprising at least one leuco composition. This application further relates to test kits for detecting authentic compositions comprising at least one leuco composition.

BACKGROUND OF THE INVENTION

The manufacture and sale of counterfeit goods is a growing problem in the consumer packaged goods industry. Counterfeit goods are generally lower quality as compared to the branded product they imitate. Counterfeit goods can be harmful to a brand by diverting profits and associating lower quality and less efficacious products with the brand's name. Counterfeit goods may also be dangerous to consumers. The use of low quality and ineffective ingredients may harm the health of consumers.

Packaging solutions have been developed to reduce the risk of counterfeit goods being sold as authentic. Such solutions include tamper-evident seals, the incorporation of holograms and color-shifting ink in label graphics, and distinctive package designs. These solutions, however, can themselves be counterfeited and are ineffective when counterfeit product is filled into an original container. Therefore, there remains an ongoing need for a rapid and easy method to detect the authenticity of a product that does not impact the quality or functionality of the product.

Therefore, it would be beneficial to provide compositions, rapid and easy methods, and test kits to detect the authenticity of products while not impacting the quality or functionality of products.

SUMMARY OF THE INVENTION

The present disclosure relates to compositions comprising at least one leuco composition, wherein the composition is a first color at any given time through manufacture, shipment, shelf storage, and normal product use. The leuco composition is capable of changing from a colorless or substantially colorless state to a colored state in the presence of a sufficient triggering agent, thereby causing the laundry care composition to change from a first color to a second color.

The present disclosure provides a composition comprising at least one laundry care ingredient and at least one leuco composition. The composition is material that is susceptible to counterfeiting, such as a perfume composition, a fuel composition, a lubricant composition, a thermoplastic polymer composition, a polyol composition, a polyurethane composition, or a seed coating composition. In a preferred embodiment, the leuco composition comprises at least one leuco compound conforming to Formula (I):

$$Ar^1Ar^2Ar^3CH \qquad (I)$$

wherein $Ar^2$ and $Ar^3$ are independently a carbocyclic aryl or heteroaryl, and $Ar^1$ is selected from the group consisting of: unsubstituted phenyl, electron deficient carbocyclic aryl, and heteroaryl.

The present disclosure also provides a method of detecting an authentic composition, the method comprising the steps of: a) providing a composition having a first color and comprising at least one leuco composition; b) adding a triggering agent to the composition, wherein the triggering agent is sufficient to effect a change in the at least one leuco composition from a colorless state to a colored state; and c) detecting a change in the composition from the first color to a second color, wherein the change from the first color to the second color is visually perceptible.

The present disclosure also provides a test kit for determining the authenticity of compositions comprising: a) a receptacle for receiving an amount of a composition; b) a triggering agent, wherein the triggering agent converts a leuco composition; and c) instructions for combining the composition and triggering agent to detect authentic compositions.

DETAILED DESCRIPTION OF THE INVENTION

Definitions

As used herein, the term "alkoxy" is intended to include $C_1$-$C_8$ alkoxy and alkoxy derivatives of polyols having repeating units such as butylene oxide, glycidol oxide, ethylene oxide or propylene oxide.

As used herein, the interchangeable terms "alkyleneoxy" and "oxyalkylene," and the interchangeable terms "polyalkyleneoxy" and "polyoxyalkylene," generally refer to molecular structures containing one or more than one, respectively, of the following repeating units: —$C_2H_4O$—, —$C_3H_6O$—, —$C_4H_8O$—, and any combinations thereof. Non-limiting structures corresponding to these groups include —$CH_2CH_2O$—, —$CH_2CH_2CH_2O$—, —$CH_2CH_2CH_2CH_2O$—, —$CH_2CH(CH_3)O$—, and —$CH_2CH(CH_2CH_3)O$—, for example. Furthermore, the polyoxyalkylene constituent may be selected from the group consisting of one or more monomers selected from a $C_{2-20}$ alkyleneoxy group, a glycidyl group, or mixtures thereof.

The terms "ethylene oxide," "propylene oxide" and "butylene oxide" may be shown herein by their typical designation of "EO," "PO" and "BO," respectively.

As used herein, the terms "alkyl" and "alkyl capped" are intended to mean any univalent group formed by removing a hydrogen atom from a substituted or unsubstituted hydrocarbon. Non-limiting examples include hydrocarbyl moieties which are branched or unbranched, substituted or unsubstituted including $C_1$-$C_{18}$ alkyl groups, and in one aspect, $C_1$-$C_6$ alkyl groups.

As used herein, unless otherwise specified, the term "aryl" is intended to include $C_3$-$C_{12}$ aryl groups. The term "aryl" refers to both carbocyclic and heterocyclic aryl groups.

As used herein, the term "alkaryl" refers to any alkyl-substituted aryl substituents and aryl-substituted alkyl substituents. More specifically, the term is intended to refer to $C_{7-16}$ alkyl-substituted aryl substituents and $C_{7-16}$ aryl substituted alkyl substituents which may or may not comprise additional substituents.

As used herein, the term "detergent composition" is a sub-set of laundry care composition and includes cleaning compositions including but not limited to products for laundering fabrics. Such compositions may be pre-treatment composition for use prior to a washing step or may be rinse added compositions, as well as cleaning auxiliaries, such as bleach additives and "stain-stick" or pre-treat types.

As used herein, the term "laundry care composition" includes, unless otherwise indicated, granular, powder, liquid, gel, paste, unit dose, bar form and/or flake type washing agents and/or fabric treatment compositions, including but not limited to products for laundering fabrics, fabric softening compositions, fabric enhancing compositions, fabric freshening compositions, and other products for the care and maintenance of fabrics, and combinations thereof. Such compositions may be pre-treatment compositions for use prior to a washing step or may be rinse added compositions, as well as cleaning auxiliaries, such as bleach additives and/or "stain-stick" or pre-treat compositions or substrate-laden products such as dryer added sheets.

As used herein, the term "leuco" (as used in reference to, for example, a compound, moiety, radical, dye, monomer, fragment, or polymer) refers to an entity (e.g., organic compound or portion thereof) that, upon exposure to specific chemical or physical triggers, undergoes one or more chemical and/or physical changes that results in a shift from a first color state (e.g., uncolored or substantially colorless) to a second more highly colored state. Suitable chemical or physical triggers include, but are not limited to, oxidation, pH change, temperature change, and changes in electromagnetic radiation (e.g., light) exposure. Suitable chemical or physical changes that occur in the leuco entity include, but are not limited to, oxidation and non-oxidative changes, such as intramolecular cyclization. Thus, in one aspect, a suitable leuco entity can be a reversibly reduced form of a chromophore. In one aspect, the leuco moiety preferably comprises at least a first and a second $\pi$-system capable of being converted into a third combined conjugated $\pi$-system incorporating said first and second $\pi$-systems upon exposure to one or more of the chemical and/or physical triggers described above.

As used herein, the terms "leuco composition" or "leuco colorant composition" refers to a composition comprising at least two leuco compounds having independently selected structures as described in further detail herein.

As used herein "average molecular weight" of the leuco colorant is reported as a weight average molecular weight, as determined by its molecular weight distribution: as a consequence of their manufacturing process, the leuco colorants disclosed herein may contain a distribution of repeating units in their polymeric moiety.

As used herein, the terms "maximum extinction coefficient" and "maximum molar extinction coefficient" are intended to describe the molar extinction coefficient at the wavelength of maximum absorption (also referred to herein as the maximum wavelength), in the range of 400 nanometers to 750 nanometers.

As used herein, the term "first color" is used to refer to the color of the laundry care composition before triggering, and is intended to include any color, including colorless and substantially colorless.

As used herein, the term "second color" is used to refer to the color of the laundry care composition after triggering, and is intended to include any color that is distinguishable, either through visual inspection or the use of analytical techniques such as spectrophotometric analysis, from the first color of the laundry care composition.

As used herein, the term "converting agent" refers to any oxidizing agent as known in the art other than molecular oxygen in any of its known forms (singlet and triplet states).

As used herein, the term "triggering agent" refers to a reactant suitable for converting the leuco composition from a colorless or substantially colorless state to a colored state.

As used herein, the term "whitening agent" refers to a dye or a leuco colorant that may form a dye once triggered that when on white cotton provides a hue to the cloth with a relative hue angle of 210 to 345, or even a relative hue angle of 240 to 320, or even a relative hue angle of 250 to 300 (e.g., 250 to 290).

As used herein, "cellulosic substrates" are intended to include any substrate which comprises at least a majority by weight of cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Articles formed from cellulosic fibers include textile articles such as fabrics. Articles formed from pulp include paper.

As used herein, articles such as "a" and "an" when used in a claim, are understood to mean one or more of what is claimed or described.

As used herein, the terms "include/s" and "including" are meant to be non-limiting.

As used herein, the term "solid" includes granular, powder, bar and tablet product forms.

As used herein, the term "fluid" includes liquid, gel, paste and gas product forms.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

As used herein, the term "electron deficient carbocyclic aryl group" refers to $C_3$-$C_{12}$ carbocyclic aryl groups with an electron withdrawing substituent covalently bonded to the aryl group.

As used herein, unless otherwise specified, the term "heteroaryl" refers to $C_3$-$C_{12}$ aryl groups wherein at least one ring carbon has been replaced with a heteroatom selected from —O—, —S—, —N═, —N(R)—, and mixtures thereof, wherein R is not hydrogen.

The term "substituted heteroaryl" refers to $C_3$-$C_{12}$ aryl groups, wherein at least one ring carbon has been replaced with a heteroatom selected from —O—, —S—, —N═, —N(R)—, and mixtures thereof, and wherein an atom or group other than a hydrogen is covalently bonded to the any ring atom of the heteroaryl.

As used herein, the term "electron donating substituent" refers to an atom or functional group that donates some of its electron density into a conjugated $\pi$ system via resonance or inductive effects, thus making the π system more nucleophilic. When attached to a benzene molecule, an electron donating substituent makes it more likely to participate in electrophilic substitution reactions. Benzene itself will normally undergo substitutions by electrophiles, but additional substituents can alter the reaction rate or products by electronically or sterically affecting the interaction of the two reactants. Electron donating substituents are often known as activating groups. Suitable electron donating substituents include but are not limited to tertiary amines (—NR$_2$), secondary amines (—NHR), primary amines (—NH$_2$), ethers (—OR), thioethers (—SR) hydroxy (—OH), thiols (—SH), amides (—NHC(O)R), esters (—OC(O)R), alkyl (—R), phenyl (—C$_6$H$_5$), and vinyl e.g., (—CH=CH$_2$, —CH=CHR, —CR=CH$_2$, —CR=CHR), wherein R represents an organic radical.

As used herein, the term "electron withdrawing substituent" refers to an atom or functional group that removes electron density from a π system, making the π system more electrophilic. When attached to a benzene molecule an electron withdrawing substituent makes electrophilic aromatic substitution reactions slower and more complex. Electron withdrawing substituents are often called deactivating groups. Suitable electron withdrawing substituents include but are not limited to trihalides (e.g., —CF$_3$, —CCl$_3$), cyano (—CN), sulfonates (—SO$_3$H), sulfonate esters (—SO$_3$R), sulfones (—SO$_2$R), sulfoxides (—S(O)R), ammonium (—NH$_3$+), quaternary amines (—NR$_3$+), nitro (—NO$_2$), aldehydes (—C(O)H), ketones (—C(O)R), carboxylic acid (—COOH), carboxylic acid esters (—C(O)OR), acyl chloride (—C(O)C$_1$), amides (—C(O)NH$_2$, —C(O)NHR, —C(O)NR$_2$), and halides (e.g., F). In cases where a carbocyclic aryl group has multiple substituents present, and the substituents are a mixture of electron withdrawing and electron donating substituent groups, or the structures of the substituents are unknown, determination of whether the carbocyclic aryl group is electron deficient may be made by following the method "Determination of Electron Deficient Carbocyclic Aryl Ring," as presented herein. The method is only followed where there are mixtures of electron withdrawing and electron donating substituents.

Compositions

The present disclosure relates to compositions comprising leuco compositions. Leuco dyes are known to exhibit a change from a colorless or slightly colored state to a colored state upon exposure to specific chemical or physical triggers. The change in coloration that occurs is typically visually perceptible to the human eye. The color change upon triggering stems from the change of the molar attenuation coefficient (also known as molar extinction coefficient, molar absorption coefficient, and/or molar absorptivity in some literatures) of the leuco dye molecule in the 400-750 nm range.

Leuco dyes are also known as, for example, bluing or hueing agents that may be capable of masking the yellowing of fabrics. These leuco dyes are able to change from a first color to a second color during the laundering process. These leuco dyes are also capable of deposition onto fabric, allowing for the whitening effect.

While traditional leuco dyes can be effective for the purposes stated above, they are inappropriate for use as anti-counterfeiting agents because they can change from the first color state to the second color state over time and thereby alter the appearance and functionality of the product to which they are added.

It has now surprisingly been found that compositions containing the presently claimed leuco compositions undergo a color change only when contacted with a sufficient triggering agent. As such, the leuco compositions do not impact the quality or functionality of the composition through manufacture, shipment, shelf storage, or during use; but only when tested for authenticity. Additionally, the leuco composition may not deposit onto fabric, thereby retaining the composition's appropriateness for use with any fabric type and color.

The present disclosure relates to compositions comprising at least one leuco composition. In a preferred aspect, the leuco composition comprises at least one leuco compound conforming to Formula (I):

$$Ar^1Ar^2Ar^3CH \qquad (I)$$

wherein $Ar^2$ and $Ar^3$ are independently a carbocyclic aryl or heteroaryl, and $Ar^1$ is selected from the group consisting of: unsubstituted phenyl, electron deficient carbocyclic aryl, and heteroaryl. $Ar^1$ is preferably selected from the group consisting of unsubstituted phenyl, nitro-substituted carbocyclic aryl, furan, thiophene, pyridine, and indole. More preferably, $Ar^1$ is furan. The representation of Formula (I) above does not infer or in any way limit the arrangement of the substituent Ar groups.

The compositions may comprise at least one leuco composition conforming to Formula (I), as described above, wherein at least one of $Ar^2$ and $Ar^3$ is a phenyl ring substituted with an electron-donating group. The electron donating group is preferably a substituted amine covalently bonded to the phenyl ring at a position para to the carbon atom connecting the three Ar groups. More preferably, the substituted amine conforms to the formula —NR$^4$R$^5$, wherein each $R^4$ and $R^5$ are independently selected from H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, polyoxyalkylene, and mixtures thereof.

Even more preferably, the compositions may comprise at least one leuco composition conforming to Formula (I), as described above, wherein both $Ar^2$ and $Ar^3$ are phenyl rings with independently selected substituted amines covalently bonded to each phenyl ring at a position para to the carbon atom connecting the three Ar groups. The substituted amines may conform to the formula —NR$^4$R$^5$, wherein each $R^4$ and $R^5$ are independently selected from H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, polyoxyalkylene, and mixtures thereof.

The compositions described above may comprise at least one leuco composition conforming to Formula (I), as described above, and may resist deposition onto textiles. The leuco compositions may resist deposition onto textiles by, for example, having increased solubility in wash water. Where the leuco composition's affinity for the wash water is greater than its affinity for textiles, the leuco composition will have a low substantivity to textiles. The leuco composition may therefore comprise solubility-enhancing substituents. Such polar solubilizing groups may include both nonionic and ionic polar solubilizing groups.

Solubility-enhancing substituents may include substituted amines conforming to the formula —NR$^4$R$^5$, as described above, wherein at least one of $R^4$ and $R^5$ is a polyoxyalkylene. At least two, at least three, and four of $R^4$ and $R^5$ may be polyoxyalkylenes. The polyoxyalkylene or polyoxyalkylenes may be a polyoxyethylene polymer having 2-300 ethylene oxide repeating units. The polyoxyalkylene is preferably a polyoxyethylene polymer having 2-100 ethylene oxide repeating units. More particularly preferred is a polyoxyethylene polymer or polymers having 2-50 ethylene oxide repeating units. It is preferable that at least one polyoxyalkylene polymer has at least three oxyalkylene, preferably ethylene oxide, repeating units.

The polyoxyalkylene or polyoxyalkylenes may also be represented by Formula (II):

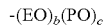 (II)

wherein the polyoxyalkylene comprises b ethylene oxide units and c propylene oxide units in any sequence, with one such unit being bound covalently to the nitrogen atom of the polyoxyalkylene substituted-amine. Preferably an ethylene oxide ("EO") unit is covalently bonded to the nitrogen atom of the polyoxyalkylene-substituted amine. The index b ranges from 2-300, preferably from 2-100, and more preferable from 2-15; and the index c represents the number of propyleneoxy ("PO") units (if any) in the polyoxyalkylene and ranges from 0 to 60, preferably from 0-20, and more preferably from 0-10.

The leuco composition's substantivity to textiles may be measured by the mole % of leuco composition that deposits onto the textile during a typical wash cycle. During a typical wash cycle, less than 10 mole % leuco composition of the laundry care composition deposits onto textiles, preferably less than 5 mole %, more preferably less than 1 mole %, and even more preferably less than 0.5 mole %.

It may be acceptable for the leuco composition to substantially deposit onto textiles during a typical wash cycle. The leuco composition's resistance to conversion from a colorless or substantially colorless state to a colored state in the absence of a sufficient triggering agent may render deposition onto textiles invisible to the user. Therefore, the leuco composition's substantivity to textiles may be greater than 10 mole %, greater than 15 mole %, and even greater than 25 mole %.

The leuco compositions of the present disclosure may include those having the formula (III):

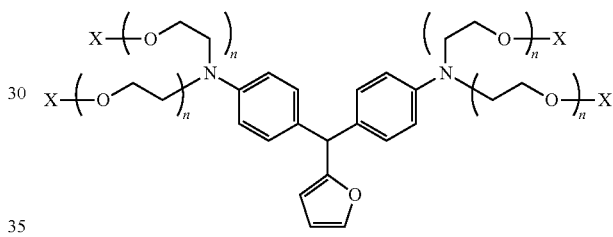 (III)

wherein both $Ar^2$ and $Ar^3$ are phenyl rings with independently selected substituted amines $—NR^4R^5$ covalently bonded to each phenyl ring at a position para to the carbon atom connecting the three Ar groups. $Ar^1$ is preferably an electron deficient carbocyclic aryl, wherein the index a is an integer from 1 to 5.

The leuco compositions of the present disclosure more preferably include those having the formula (IV):

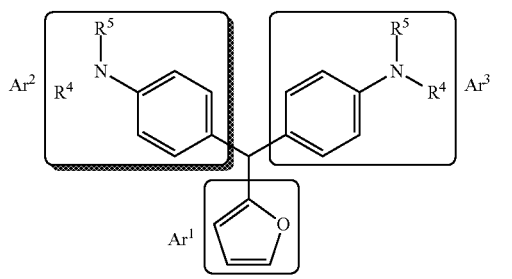 (IV)

wherein $Ar^1$ is a furan and both $Ar^2$ and $Ar^3$ are phenyl rings with independently selected substituted amines $—NR^4R^5$ covalently bonded to each phenyl ring at a position para to the carbon atom connecting the three Ar groups.

Even more preferably, the leuco compositions of the present disclosure include those having the formula (IV):

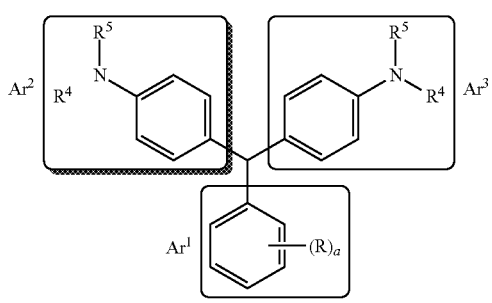 (IV)

wherein each n is independently an integer from 2 to about 300, more preferably from 2 to about 100, even more preferably from 2 to 50, most preferably each n is independently an integer from 2 to about 25; and each X is independently selected from the group consisting of H, alkyl, alkylcarboxylate and arylcarboxylate. More preferably each X is H.

The amount of leuco colorant used in the compositions of the present invention may be any level suitable to achieve the aims of the invention. In one aspect, the composition comprises leuco colorant in an amount from about 0.0001 wt % to about 1.0 wt %, preferably from 0.0005 wt % to about 0.5 wt %, even more preferably from about 0.0008 wt % to about 0.2 wt %, most preferably from 0.004 wt % to about 0.1 wt %.

In another aspect, the composition comprises leuco colorant in an amount from 0.0025 to 5.0 milliequivalents/kg, preferably from 0.005 to 2.5 milliequivalents/kg, even more preferably from 0.01 to 1.0 milliequivalents/kg, most preferably from 0.05 to 0.50 milliequivalents/kg, wherein the units of milliequivalents/kg refer to the milliequivalents of leuco moiety per kg of the composition. For leuco colorants comprising more than one leuco moiety, the number of milliequivalents is related to the number of millimoles of the leuco colorant by the following equation: (millimoles of leuco colorant)×(no. of milliequivalents of leuco moiety/millimole of leuco colorant)=milliequivalents of leuco moiety. In instances where there is only a single leuco moiety per leuco colorant, the number of milliequivalents/kg will be equal to the number of millimoles of leuco colorant/kg of the composition.

The molar extinction coefficient of said colored state at the maximum absorbance in the wavelength in the range 200 to 1,000 nm (more preferably 400 to 750 nm) is preferably at least five times, more preferably 10 times, even more preferably 25 times, most preferably at least 50 times the molar extinction coefficient of said colorless state at the wavelength of the maximum absorbance of the colored state. Preferably, the molar extinction coefficient of said colored state at the maximum absorbance in the wavelength in the range 200 to 1,000 nm (more preferably 400 to 750 nm) is at least five times, preferably 10 times, even more preferably 25 times, most preferably at least 50 times the maximum molar extinction coefficient of said colorless state in the corresponding wavelength range. An ordinarily skilled artisan will realize that these ratios may be much higher. For example, the colorless state may have a maximum molar extinction coefficient in the wavelength range from 400 to 750 nm of as little as 10 $M^{-1}cm^{-1}$, and the colored state may have a maximum molar extinction coefficient in the wavelength range from 400 to 750 nm of as much as 80,000 $M^{-1}cm^{-1}$ or more, in which case the ratio of the extinction coefficients would be 8,000:1 or more.

The maximum molar extinction coefficient of said colorless state at a wavelength in the range 400 to 750 nm is less than 1000 $M^{-1}cm^{-1}$, and the maximum molar extinction coefficient of said colored state at a wavelength in the range 400 to 750 nm is more than 5,000 $M^{-1}cm^{-1}$, preferably more than 10,000, 25,000, 50,000 or even 100,000 $M^{-1}cm^{-1}$. A skilled artisan will recognize and appreciate that a polymer comprising more than one leuco moiety may have a significantly higher maximum molar extinction coefficient in the colorless state (e.g., due to the additive effect of a multiplicity of leuco moieties or the presence of one or more leuco moieties converted to the colored state).

The colored state of the leuco compositions may have a maximum absorbance ($\lambda_{max}$) at a wavelength of 400-700 nm. Preferably, the $\lambda_{max}$ of the colored state of the leuco compositions may be outside the range of 520-620 nm. More preferably, the $\lambda_{max}$ of the colored state of the leuco compositions may be 625-655 nm.

The compositions of the invention can be any composition or product that is susceptible to counterfeiting. Suitable examples of such compositions or products include, but are not limited to, branded consumer products and branded intermediate goods. In a preferred embodiment, the invention provides a perfume composition, a fuel composition, a lubricant composition, a thermoplastic polymer composition, a polyol composition, a polyurethane composition, or a seed coating composition.

A perfume composition according to the invention can comprise any suitable perfume ingredients. A typical perfume or fragrance is composed of "top notes" of perfumes and bottom notes of perfumes. A top note of perfume are the perfuming ingredients which are perceived immediately upon the application of a perfume, while the bottom notes are the ingredients which are perceived long after application. In addition to the top and bottom notes of perfumes, perfumery adjuvants are also used to impart additional benefit such as color, a particular light resistance, chemical stability, etc. A detailed description of the nature and type of adjuvant commonly used in perfuming bases cannot be exhaustive, but the said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidants heat/light and or buffers or chelating agents, such as BHT), color agents (e.g. dyes and/or pigments), preservative (e.g. antibacterial or antimicrobial or antifungal or anti irritant agents), abrasives, skin cooling agents, fixatives, insect repellents, ointments, vitamins and mixture thereof. Other suitable perfumery adjuvant optionally used can be tertiary amines, and alcohols, in particular those with high water solubility such as triethanolamine, methyldiethylamine, methyldiethanolamine, ethanol, propanol etc. In conjunction to the above ingredients, the leuco composition and leuco compounds described above can be added to the perfume composition in an amount of 0.001 to 1 wt %, preferably from 0.001 to 0.5% and most preferably from 0.001 to 0.1%.

A fuel composition according to the invention can comprise any suitable fuel ingredients. Suitable fuel compositions include, but are not limited to, gasoline, diesel, kerosene, bio-diesel, or other alcohol based fuels. The leuco composition can be added to the fuel composition in an amount of from 0.001 to 1 wt %, preferably from 0.001 to 0.5% and most preferably from 0.001 to 0.1%. The fuel composition may further comprise other additives such as anti-knocking agents, methylcyclopentadienyl manganese tricarbonyl, antioxidants, metal deactivators, detergents, and alcohols.

A lubricant composition according to the invention can comprise any suitable lubricant ingredients. Suitable lubricant compositions include, but are not limited to, engine oil, automatic transmission fluid, gear oil, hydraulic fluid, turbine oil, transformer oil, and compressor oil. The leuco composition and leuco compounds described above can be added to the lubricant composition in an amount from 0.001 to 1 wt %, preferably from 0.001 to 0.5% and most preferably from 0.001 to 0.1%. The lubricant compositions may further comprise other additives such as dispersants, antioxidants, anti-wear agents, detergents, corrosion inhibitors, metal deactivators, viscosity modifiers, and friction modifiers.

A thermoplastic polymer composition according to the invention can comprise any suitable thermoplastic polymer and thermoplastic polymer additives. Suitable thermoplastic polymers include, but are not limited to, polyesters, polyamides, polyolefins, acrylics, acrylonitrile butadiene styrene, polylactic acid, polybenzimidazoles, polycarbonates, polyether sulfones, polyoxymethylenes, polyetherether ketones, polyetherimides, polyphenylene oxides, polyphenylene sulfides, polyvinyl chlorides, polytetrafluoroethylenes, and polystyrenes. Suitable polyolefins include, but are not limited to, polyethylene, polypropylene, polymethylpentene, and polybut-1-ene. The thermoplastic compositions may further comprise other additives such as antioxidants, nucleating agents, clarifying agents, UV absorbers, photo stabilizers, fillers, lubricants, acid scavengers, anti-static agents, pigments and/or dyes.

A polyol composition according to the invention can comprise any suitable polyol and polyol additives. Suitable polyols include, but are not limited to, polyester polyols, polyether polyols and mixtures of the two.

A polyurethane composition according to the invention can comprise any suitable polyurethane and polyurethane additives. Polyurethane products are produced through the catalyzed polymerization of the reaction products of polyols and isocyanates. Typical polyols include both polyester polyols, polyether polyols and mixtures of the two. TDI (toluene diisocyanate) and MDI (methylene diphenyl diisocyanate) are two aromatic isocyanates, whereas HDI (hexamethylene diisocyanate) is the aliphatic isocyanate that are most commonly used in the polyurethane industry. Auxiliary blowing agents such as methylene chloride, acetone, carbon dioxide, can be used when making polyurethane foam for blowing capability. Other additives such as UV absorbers and antioxidants to protect the polyurethane product from degradation due to light and/or oxygen is also used.

A seed coating composition according to the invention can comprise any suitable seed coating ingredients. Suitable seed coating ingredients include, but are not limited to, binders, active ingredients (plant enhancing additives and/or plant protective additives) insecticides, fungicides, nematocides, flow agents, colorants, pearlescent agents, wetting agents, dispersing agents, thickening agents, anti-foam agents, surfactants, and solvents. Suitable examples of such seed coating ingredients are disclosed in, for example, United States Patent Application Publication No. US 2017/0127670 A1 (Bueno et al.), the disclosure of which is hereby incorporated by reference.

Triggering Agent

As used herein, a triggering agent is a reactant suitable for converting the leuco composition from a colorless or substantially colorless state to a colored state. Triggering agents suitable for use are any oxidizing agent as known in the art other than atmospheric concentrations of molecular oxygen in its native (triplet) state. A commercial good, such as a laundry care composition, would encounter such molecular oxygen concentrations during manufacture, distribution through a supply chain (including shipment by car, truck, rail, boat, and airplane with or without temperature controls), shelf life storage, or normal use as directed by on-pack instructions. The term "sufficient triggering agent" also does not refer to oxidants at concentrations found in sources (e.g., municipal water supplies) that would contact or be mixed with the composition during normal use The triggering agent may be a halogen bleach compound that is a solid at 25° C. Suitable hypochlorite generating compounds are those water soluble dry solid materials which generate hypochlorite ion on contact with, or dissolution in, water. Non-limiting examples thereof are the dry, particulate heterocyclic N-chlorimides such as trichlorocyanuric acid, dichlorocyanuric acid and salts thereof such as sodium dichlorocyanurate and potassium dichlorocyanurate. Other N-chloroimides may be used such as N-chlorosuccinimide, N-chloromalonimide, N-chlorophthalimide and N-chloronaphthalimide. Additional suitable N-chloroimides are the hydantoins such as: 1,3-dichloro-5,5-dimethylhydantion; N-monochloro-C,C-dimethylhydantion; methylene-bis (N-chloro-C,C-dimethylhydantoin); 1,3-dichloro-5-methyl-5-isobutylhydantoin; 1,3-dichloro-5-methyl-5-ethylhydantoin; 1,3-dichloro-5,5-diisobutylhydantoin; 1, 3-dichloro-5-methyl-5-n-amylhydantoin; and the like. Other useful hypochlorite-liberating agents are trichloromelamine and dry, particulate, water soluble anhydrous inorganic salts such as calcium hypochlorite, calcium hypochlorite tetrahydrate, and lithium hypochlorite.

The triggering agent may be selected from the group consisting of dichloroisocyanuric acid, alkali metal dichloroisocyanurates, which may be anhydrous or can be used in the form of its mono- and/or dihydrates, 1,3,5-trichloroisocyanuric acid, alkali metal 1,3,5-trichloroisocyanurates, N-chlorosulfonamides such as alkali metal N-chloro(4-methylbenzene)sulfonamide (Chloramine® T), N-chlorosulfamate, N-halosuccinimides such as N-chlorosuccinimide and/or N-bromosuccinimide, calcium oxychloride, which can also be used as its mixed salt with calcium chloride and calcium hydroxide, such as 3 CaCl(OCl).Ca(OH)$_2$.5 H$_2$O, and its mixtures. Preferred solid halogen bleach compounds suitable for use as triggering agents are alkali metal dichloroisocyanurates. Sodium is the preferred alkali metal, although lithium and potassium salts may also be used.

Hydride donors may be used as the triggering agent. Suitable hydride donors may be selected from the group consisting of chloranil (tetrachloro-1,4-benzoquinone), tetrachloro-1,2-benzoquinone, DDQ (2,3-Dichloro-5,6-dicyano-p-benzoquinone) and mixtures thereof.

Highly preferred triggering agents for use in the present invention include sodium hypochlorite, calcium hypochlorite, sodium dichlorocyanurate, alkali metal N-chloro(4-methylbenzene) sulfonamide (Chloramine® T), N-chlorosulfamate, N-bromosuccinimide, tetrachloro-1,2-benzoquinone, DDQ (2,3-Dichloro-5,6-dicyano-p-benzoquinone) and mixtures thereof.

Triggering agents may be liquid or solid. Triggering agents may be pre-packaged into single dose aliquots. Triggering agents may also be in the form of tablets.

Product Forms

Liquid

When in the form of a liquid, the laundry care compositions may be aqueous (typically above 2 wt % or even above 5 or 10 wt % total water, up to 90 or up to 80 wt % or 70 wt % total water) or non-aqueous (typically below 2 wt % total water content). The compositions may be in the form of an aqueous solution or uniform dispersion or suspension of surfactant, leuco composition, and certain optional other ingredients. Some of the ingredients may normally be in solid form and be combined with the normally liquid components of the composition, such as the liquid alcohol ethoxylate nonionic and the aqueous liquid carrier. Such a solution, dispersion or suspension may be acceptably phase stable. When in the form of a liquid, the laundry care compositions may have viscosity from 1 to 1500 centipoises (1-1500 mPa*s), preferably from 100 to 1000 centipoises (100-1000 mPa*s), and most preferably from 200 to 500 centipoises (200-500 mPa*s) at 20 s-1 and 21° C. Viscosity can be determined by conventional methods. Viscosity is measured using an AR 550 rheometer from TA instruments using a plate steel spindle at 40 mm diameter and a gap size of 500 μm. The high shear viscosity at 20 s-1 and low shear viscosity at 0.05-1 can be obtained from a logarithmic shear rate sweep from 0.1-1 to 25-1 in 3 minute's time at 21° C. The preferred rheology described therein may be achieved using internal existing structuring with detergent ingredients or by employing an external rheology modifier. Liquid detergent compositions may have a high shear rate viscosity of from about 100 centipoise to 1500 centipoise, more preferably from 100 to 1000 cps. Laundry softening compositions may have high shear rate viscosity of from 10 to 1000, more preferably from 10 to 800 cps, most preferably from 10 to 500 cps.

The laundry care composition can be prepared by combining the components thereof in any convenient order and by mixing, e.g., agitating, the resulting component combination to form a phase stable liquid laundry care composition. In a process for preparing such compositions, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture may be continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills, may be incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture may be continued for a period of time sufficient to form compositions having the requisite viscosity and phase stability characteristics. Frequently this will involve agitation for a period of from about 30 to 60 minutes.

The liquid laundry detergent composition may comprise less than about 50%, or even less than about 40% or even less than about 30% by weight of water. The liquid laundry detergent composition may comprise from about 1% to about 30%, or even from about 2% to about 20% or even from about 3% to about 15% by weight of the composition of water. The water and other components in the laundry care composition may be free of any triggering agent.

Pouches

The laundry care composition may be provided in the form of a unitized dose, either tablet form or preferably in the form of a liquid/solid (optionally granules)/gel/paste held within a water-soluble film in what is known as a pouch or pod. The laundry care composition can be encapsulated in a single or multi-compartment pouch or pod. Multi-compartment pouches are described in more detail in EP-A-2133410. When the laundry care composition is present in a multi-compartment pouch, it may be in one or two or more compartments, thus the leuco composition may be present in one or more compartments, optionally all compartments. Non-shading dyes or pigments or other aesthetics may also be used in one or more compartments. The composition may be present in a single compartment of a multi-compartment pouch. The leuco composition may also be incorporated into the film material of the pouch.

Preferred film materials are polymeric materials. The film material can be obtained, for example, by casting, blow-molding, extrusion or blown extrusion of the polymeric material, as known in the art. Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan and carrageenan. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60 wt %. The polymer can have any weight average molecular weight, preferably from about 1000 to 1,000,000, more preferably from about 10,000 to 300,000 yet more preferably from about 20,000 to 150,000. Mixtures of polymers can also be used as the pouch material. This can be beneficial to control the mechanical and/or dissolution properties of the compartments or pouch, depending on the application thereof and the required needs. Suitable mixtures include, for example, mixtures wherein one polymer has a higher water-solubility than another polymer, and/or one polymer has a higher mechanical strength than another polymer. Also suitable are mixtures of polymers having different weight average molecular weights, for example, a mixture of PVA or a copolymer thereof of a weight average molecular weight of about 10,000-40,000, preferably around 20,000, and of PVA or copolymer thereof, with a weight average molecular weight of about 100,000 to 300,000, preferably around 150,000. Also suitable herein are polymer blend compositions, for example comprising hydrolytically degradable and water-soluble polymer blends such as polylactide and polyvinyl alcohol, obtained by mixing polylactide and polyvinyl alcohol, typically comprising about 1-35% by weight polylactide and about 65% to 99% by weight polyvinyl alcohol. Preferred for use herein are polymers which are from about 60% to about 98% hydrolysed, preferably about 80% to about 90% hydrolysed, to improve the dissolution characteristics of the material.

Different film material and/or films of different thickness may be employed in making the compartments. A benefit in selecting different films is that the resulting compartments may exhibit different solubility or release characteristics.

Most preferred film materials are PVA films known under the MonoSol trade reference M8630, M8900, H8779, those described in U.S. Pat. Nos. 6,166,117 and 6,787,512, and PVA films of corresponding solubility and deformability characteristics.

Laundry Care Components.

The laundry care composition may comprise surfactants, anionic surfactants, non-ionic surfactants, cationic surfactants, polyethylene glycol polymers, ethoxylated polyethyleneimines, rheology modifier, hueing dyes, dye transfer inhibiting agents, aesthetic colorants, encapsulates, perfumes, perfume microcapsules, perfume delivery systems, malodor reduction materials, fabric softeners, chelating agents, enzymes, enzyme stabilizers, catalytic materials, tannins, soil release polymers, silicones, polyolefin waxes, latexes, oily sugar derivatives, cationic polysaccharides, polyurethanes, fatty acids, enzyme stabilizing systems, antioxidants, opacifier, pearlescent agent, deposition aid, builder, dispersants, bleaching agent, bleach activator, bleach catalyst, organic shine polymers, surface modifying polymers, suds suppressors, metal care agents, metal salts, anti-corrosion agents, and mixtures thereof.

The laundry care composition may comprise from about 1% to about 80% by weight of the detergent or cleaning composition of a surfactant. The surfactant may be selected from the group consisting of: anionic, nonionic, amphoteric, zwitterionic, ampholytic, semi-polar, cationic surfactants, or mixtures thereof. The surfactant may be selected from the group consisting of: anionic, nonionic, cationic surfactants and mixtures thereof. The surfactant system typically comprises anionic surfactant and nonionic surfactant in a weight ratio. The weight ratio of anionic surfactant to nonionic surfactant may be from about 1.1:1 to 4:1, or preferably from about 1.2:1 to about 3:1, or preferably from about 1.5:1 to about 2.5:1, or even more preferably about 2:1.

The laundry care composition may comprise an enzyme. The enzyme may be selected from the group consisting of: hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof.

The detergent or cleaning composition may comprise a polymer. The polymer may be selected from carboxylate polymers, polyethylene glycol polymers, terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, ethoxylated polyethyleneimines and any combination thereof.

The laundry care composition may comprise other suitable components which, in some aspects, can be wholly or partially incorporated. Components may be selected according to the laundry care composition's intended function. In some aspects, in the case of multi-compartment unit dose articles, the laundry care component may be part of a non-first (e.g., second, third, fourth, etc.) composition encapsulated in compartments separate from the first laundry care composition. The non-first composition may be any suitable composition. The non-first composition may be in the form of a solid, a liquid, a dispersion, a gel, a paste or a mixture thereof. Where the unit dose comprises multiple compartments, the leuco composition may be added to or present in one, two, or even all the compartments. Concentrating an anti-oxidant with a leuco composition in a smaller volume compartment may lead to a higher local concentration of anti-oxidant which may provide enhanced stability. Therefore, as one skilled in the art would appreciate, the formulator can select the location and amount of the leuco composition according to the desired properties of the unit dose.

Method of Use.

The present disclosure also relates to a method of detecting an authentic composition. The method may include the steps of a) providing a composition having a first color comprising at least one leuco composition; b) adding a triggering agent to the composition; and c) detecting a change in the composition from the first color to a second color. The presence of the leuco composition of the claimed invention in an authentic composition can distinguish the authentic composition from a counterfeit composition. The presence of the leuco composition of the claimed invention does not impact the quality or functionality of the composition through manufacture, shipping, shelf storage, or during use.

The leuco composition changes from a colorless or substantially colorless state to a colored state upon exposure to a sufficient triggering agent. This change in the leuco composition is sufficient to impact the color of the composition, changing it from a first color to a second color. The change in color of the composition can be detected by the user, either visually or spectrophotometrically, demonstrating that the composition is authentic. A change in color of the composition can be determined following the methods presented in the Test Methods section below. A lack of color change may indicate that the composition is not authentic.

For a composition having a first color that is substantially colorless or only lightly colored, lower levels of a leuco composition may be employed. Where the composition has a first color that is more deeply colored, higher levels of leuco composition may be required to achieve a discernable change in appearance after addition of the triggering agent. If the first color state is particularly dark in color, it may be advantageous to dilute the composition with a suitable solvent or medium (for example, deionized water) before adding the triggering agent so that the change in the appearance of the diluted first color state to the second color state is more easily discerned. A change in appearance is easier to discern when comparing two samples side by side, and the instructions for detection of the change in color may include ensuring a side by side comparison of the first color and second color is performed. In other instances, side by side comparisons will not be required and a visual inspection upon adding the triggering agent will suffice to convince the one performing the detection that a significant change in appearance has occurred, establishing the product as authentic.

The method may include the steps of a) providing a composition having a first color comprising at least one leuco composition; b) adding a triggering agent to the composition, wherein the triggering agent is sufficient to effect a change in the leuco composition conforming to Formula (I), as described above, from a colorless state to a colored state; and c) detecting a change from the first color to a second color. In the method, the composition and the triggering agent can be combined in any suitable manner. For example, the composition and the coloring agent can be combined in a suitable vessel, and the color of the combined composition and triggering agent is monitored to observe any change in the color. Alternatively, the composition can be applied to a surface or substrate (e.g., a card or a test strip) on which the triggering agent is disposed. In such an embodiment, the color of the composition applied to the surface can be compared to the color of the initial composition in order to determine if any change in color has occurred.

Authentication Test Kit

Test kits may be used to detect whether a composition is authentic or counterfeit. The kits may be configured for use on-site at various facilities, such as, for example, at one or more of a customs warehouse, a retail outlet, a wholesale supply store, a manufacturing plant, a distributor, a shipping and receiving facility, a consumer's home, or any other location where a suspected counterfeit product may be found. The kit allows for rapid and effective on-site detection of counterfeit products without the need for expensive analytical instrumentation, highly trained testing technicians, or complex experimental procedures.

The test kits for detecting authentic compositions preferably includes (a) a receptacle for receiving an amount of a composition; (b) a triggering agent, wherein the triggering agent converts a leuco composition conforming to Formula (I), as described above, wherein $Ar^2$ and $Ar^3$ are independently a carbocyclic aryl or heteroaryl, and $Ar^1$ is selected from the group consisting of: unsubstituted phenyl, electron deficient carbocyclic aryl, and heteroaryl; and (c) instructions for combining the composition and triggering agent to detect an authentic compositions. The test kits may include two receptacles for receiving amounts of the composition. A second receptacle may be used for receiving an amount of the composition that can be used as a negative control, allowing for a side-by-side comparison that makes a visual determination of color change easier.

The instruction(s) for the test kits may take the form of a set of written instructions, pictorial instructions, audio instructions, video instructions, or various combinations of these instruction types. The instructions for the kits may include a color index. A color index may illustrate a range of colors that indicate an authentic composition after combination of the composition with the triggering agent. The range of colors that indicate an authentic composition will depend on the first color of the composition and the particular leuco composition chosen. In a non-limiting example, a color index having a series of green hues may be included in the instructions for a kit configured to detect the authenticity of a composition with a first color that is substantially colorless and comprises a furfural leuco composition, for example a leuco composition conforming to formula IV above, that exhibits a green color upon triggering.

The instructions may also include sample preparation directions. Sample preparation directions may instruct a user to dilute a composition sample prior to addition of the triggering agent.

Combinations

A. A composition comprising a leuco composition comprising at least one leuco composition conforming to Formula (I):

$$Ar^1Ar^2Ar^3CH \qquad (I)$$

wherein $Ar^2$ and $Ar^3$ are independently a carbocyclic aryl or heteroaryl, and wherein $Ar^1$ is selected from the group consisting of: unsubstituted phenyl, electron deficient carbocyclic aryl, and heteroaryl.

B. The composition of paragraph A, wherein $Ar^1$ is selected from the group consisting of unsubstituted phenyl, nitro-substituted carbocyclic aryl, furan, thiophene, pyridine, and indole, preferably furan.

C. The composition of any of paragraphs A, or B, wherein at least one of $Ar^2$ and $Ar^3$, preferably both $Ar^2$ and $Ar^3$, are phenyl rings substituted with an electron donating group.

D. The composition of paragraph C, wherein the electron-donating group is a substituted amine covalently bonded to the phenyl ring at a position para to the carbon atom connecting the three Ar groups.

E. The composition of paragraph D, wherein the substituted amines conform to the formula —$NR^4R^5$, and wherein each $R^4$ and $R^5$ are independently selected from the group consisting of: H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, polyoxyalkylene, and mixtures thereof.

F. The composition of paragraph E, wherein at least one $R^4$ or $R^5$ is a polyoxyalkylene comprising 3 to 60 ethylene oxide repeating units.

G. The composition of paragraph E, wherein $R^4$ and $R^5$ are polyoxyalkylenes comprising 3 to 60, preferably 10 to 25, ethylene oxide repeating units.

H. A method of detecting an authentic composition, the method comprising the steps of:
  a. providing a composition having a first color, wherein the composition comprises a leuco composition comprising at least one leuco compound that conforms to Formula (I):

$$Ar^1Ar^2Ar^3CH \qquad (I)$$

wherein $Ar^2$ and $Ar^3$ are independently carbocyclic aryl or heteroaryl, and $Ar^1$ is selected from the group consisting of: unsubstituted phenyl, electron deficient carbocyclic aryl, and heteroaryl;
  b. adding a triggering agent to the composition, wherein the triggering agent causes the at least one leuco composition to change from a colorless state to a colored state; and
  c. detecting the change, wherein the change from the first color to the second color is visually perceptible.

I. The method of paragraph I, wherein the change from the first color to the second color has a color change score (DE*) of at least 2.

J. The method of any of paragraphs I and J, wherein $Ar^1$ is selected from the group consisting of unsubstituted phenyl, nitro-substituted carbocyclic aryl, furan, thiophene, pyridine, and indole, preferably furan.

K. The method of any of paragraphs I, J, and K, wherein $Ar^2$ and $Ar^3$ are phenyl rings each with independently selected substituted amines conforming to the formula —$NR^4R^5$ covalently bonded to each phenyl ring at a position para to the carbon atom connecting the three Ar groups, and wherein each $R^3$ and $R^4$ are independently selected from H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, polyoxyalkylene, and mixtures thereof.

L. The method of any of paragraphs I, J, K, and L, wherein the triggering agent is selected from the groups consisting of: sodium hypochlorite, calcium hypochlorite, sodium dichlorocyanurate, alkali metal N-chloro(4-methylbenzene) sulfonamide, N-chlorosulfamate, N-bromosuccinimide, tetrachloro-1,2-benzoquinone, DDQ (2,3-Dichloro-5,6-dicyano-p-benzoquinone) and mixtures thereof.

M. A test kit for detecting authentic compositions comprising:
  a) a receptacle for receiving an amount of a composition;
  b) a triggering agent, wherein the triggering agent converts a leuco compound conforming to Formula (I):

$$Ar^1Ar^2Ar^3CH \qquad (I)$$

in a composition from a colorless to a colored state, wherein $Ar^2$ and $Ar^3$ are independently carbocyclic aryl or heteroaryl, and $Ar^1$ is selected from the group consisting of: unsubstituted phenyl, electron deficient carbocyclic aryl, and heteroaryl; and
  c) instructions for combining the composition and triggering agent to detect authentic compositions.

N. The test kit of paragraph N, wherein the instructions comprise a color index.

Test Methods

I. Determination of Electron Deficient Carbocyclic Aryl

Where a carbocyclic aryl group has multiple substituents or where the structure of the leuco composition is unknown, the following method can be used to determine whether a carbocyclic aryl group is electron deficient. For the purposes of the present invention, a carbocyclic aryl group is considered electron deficient if the rate of color formation on storage for the two species shown below is in the order:

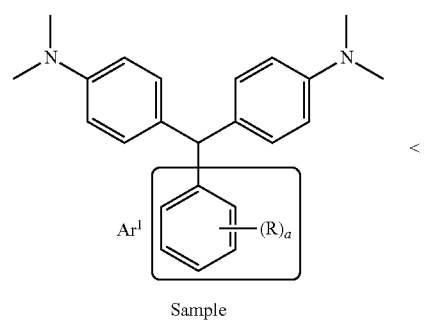

Sample

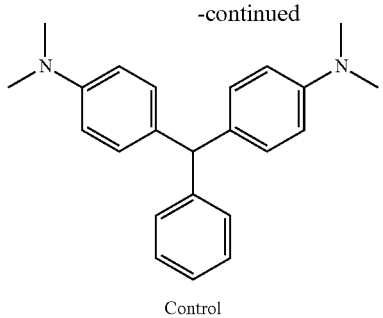

Control wherein the index a is 1 to 5 and R is not H in the sample. If the rate of the Sample composition bearing a independently selected R substituents is not less than the rate of the Control composition illustrated on the right, the carbocyclic ring ($Ar^1$) in the sample composition is not electron-deficient. The Control composition is 4,4'-(phenylmethylene)bis [N,N-dimethylbenzenamine], also known as Leucomalachite green, CAS No. 129-73-7, available for purchase from TCI America Research Chemicals, Portland, Oreg., 97203. Prepare by standard methods a Sample leuco composition and a Control leuco composition, respectively, from 2 equivalents of N,N-dimethyl aniline and the aldehydes shown below.

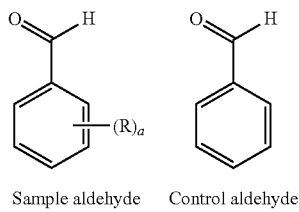

Sample aldehyde  Control aldehyde

Alternatively, the Control leuco composition may be purchased as described above. Prepare a target composition from each leuco compound, incorporating the leuco compound at $3.00 \times 10^{-4}$ moles·kg of composition. Measure the initial absorbance spectra of each composition, as well as that of a sample composition that does not contain any leuco compound, between 400 and 750 nm, using a cuvette with a path length of 1.0 cm. Determine the initial difference absorbance spectra. The initial difference absorbance spectrum for the Sample compound is found by subtracting the initial absorbance values for the nil leuco composition from the initial values for the composition containing the Sample leuco compound. The initial difference absorbance spectrum for the Control composition is found by subtracting the initial absorbance values for the nil leuco composition from the initial values for the composition containing the Control leuco compound.

Store the three samples in the dark in sealed containers at 50° C. for 12 weeks, and then remove the samples, allow to cool to room temperature, and measure the final absorbance spectra of each of the three compositions. Determine the final difference absorbance spectra for the Sample and Control in a manner analogous to the determination of the initial difference spectrum described above. Determine the change in the difference spectra from initial to final at the lambda max for each of the triphenylmethane dyes formed from the respective leuco compositions. For the control leuco composition, the triphenylmethane dye formed is Malachite green, CAS No. 14426-28-9, available for purchase from BOC Sciences, Shirley, N.Y., 11967. If a clear local absorbance maximum of at least 0.1 absorbance units is not found in the change in the difference spectra of at least one of the Sample composition or Control composition at the wavelength of their respective lambda max values, place the samples back in storage as before for an additional 4 weeks and repeat the measurements. Repeat as necessary until a local absorbance maximum of at least 0.1 absorbance units is found in the change in the difference spectra at least one of the Sample composition or Control composition at the wavelength of their respective lambda max values.

At the point where the change in the difference absorbance spectrum of at least one of the Sample composition or the Control composition has a clear local absorbance maximum of at least 0.1 absorbance units, compare the two values of absorbance at the individual lambda max of the triphenylmethane dyes formed from the respective leuco compositions. If the difference in absorbance spectrum for the composition with the Sample leuco composition has a lower absorbance at the lambda max for the triphenylmethane dye formed from the Sample leuco composition than absorbance at the lambda max for the triphenylmethane dye (Malachite green) formed from the Control leuco colorant composition in the difference absorbance spectrum for the composition with the Control leuco colorant composition, then the aryl ring comprising the a independently selected R substituents in the Sample leuco colorant composition is considered to be electron deficient.

II. Detection of Change in Color of a Composition

A change from a first color to a second color in the composition of the present disclosure may be detected using any suitable method, including visual or spectrophotometric methods.

Changes in color of the composition may be detected by spectrophotometric analysis as described below. The L*, a*, and b* values of a sample of composition before and after addition of a triggering agent are collected. The color change score (DE*) is calculated using the following equation:

$$DE^* = ((L^*_i - L^*_f)^2 + (a^*_i - a^*_f)^2 + (b^*_i - b^*_f)^2)^{1/2}$$

where the subscripts i and f refer to the composition before addition of the triggering agent (the first, or initial (i), color), and the composition after addition of the triggering agent (the second, or final (f), color), respectively.

Depending on the first color of the composition, a change in the color of a composition from a first color to a second color may be visually perceptible at a DE*=2.0 or larger, especially when the first color and second color are compared side by side. In some cases, it may be preferable to adjust the amount of leuco composition employed in the composition such that the change in color (DE*) between the first color and the second color is at least about 5, or even at least about 10. This ensures that the color change is easily discernable by visual inspection and enhances certainty in distinguishing an authentic product from an inauthentic product.

Such factors are well known to those skilled in the art and it is a routine matter for the formulator to select a leuco composition, incorporate the leuco composition at an appropriate level into the laundry care formulation, select a suitable triggering agent, and develop easily understood and easily followed instructions for the detection of a change in color.

Spectrophotometric Analysis for Determining L*, a*, b*, Chroma (C*), and Hue (h*) of a Composition:

The aesthetic appearance of a composition is measured on a LabScan XE reflectance spectrophotometer (HunterLabs, Reston, Va.; D65 illumination, 10° observer, UV light excluded) utilizing the Translucent Sample Set (Part no.

LSXE-SC-ASSY) including sample cup, ring and disk set, sample cup port insert, and opaque cover. Step by step instructions are found in Hunter Labs Applications Note, Vol. 11, No. 3, 2008.

The purpose of the ring and disk set is to control the liquid characteristics and extra light interactions (diffusion and transmission) associated with translucent liquid samples, thus making these samples more like the opaque samples the sensor was designed to measure.

When the ring and disk set is used to measure a liquid, the black plastic ring is first placed in the sample cup to fix the internal path length of light through the liquid sample to 10 mm while excluding outside light that can cause measurement interference. The liquid is poured into the cup until the level of liquid is higher than the top of the black ring.

The white ceramic disk is lowered into the liquid until it sits on top of the ring. The disk provides a white background to direct light that has traveled through the liquid back to the detector. A black sample cup cover is then placed over the sample cup to prevent any ambient light from outside the instrument from leaking into the detector. The liquid sample is measured through the bottom of an excellent optical-quality quartz sample cup as part of the ring and disk set, and is used with the accompanying port insert. Step-by-step instructions for using the ring and disk set are provided below.

1. Orient the instrument so that the sample port is facing up. Replace the regular port insert with the special port insert for the sample cup.
2. Standardize the instrument with the special port insert in place.
3. Insert the 10-mm black ring into the cup so that it settles flat on the bottom of the cup.
4. Fill the cup with the liquid sample until the liquid is above the level of the ring.
5. Float the white ceramic disk down through the liquid sample until it rests firmly on top of the black float ring. The goal is to have the sample appear smooth and opaque through the glass bottom of the sample cup.
6. Place the sample cup at the instrument port and cover it with the opaque cover.
7. Measure the sample and record the color values.
8. Pour the sample out of the sample cup, refill it, and measure again. Averaging of three readings with replacement of the liquid between readings is required.

FORMULATION EXAMPLES

The following are illustrative examples of laundry care compositions according to the present disclosure and are not intended to be limiting.

Examples 1-7: Heavy Duty Liquid Laundry Detergent Compositions

| Ingredients | 1 | 2 | 3 | 4 | 5 | 6 | 7 |
| --- | --- | --- | --- | --- | --- | --- | --- |
| | | | | % weight | | | |
| $AE_{1.8}S$ | 6.77 | 5.16 | 1.36 | 1.30 | — | — | — |
| $AE_3S$ | — | — | — | — | 0.45 | — | — |
| LAS | 0.86 | 2.06 | 2.72 | 0.68 | 0.95 | 1.56 | 3.55 |
| HSAS | 1.85 | 2.63 | 1.02 | — | — | — | — |
| AE9 | 6.32 | 9.85 | 10.20 | 7.92 | — | — | — |
| AE8 | | | | | | | 35.45 |
| AE7 | | | | | 8.40 | 12.44 | |
| $C_{12-14}$ dimethyl Amine Oxide | 0.30 | 0.73 | 0.23 | 0.37 | — | — | — |
| $C_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI | 0.32 | 0.05 | — | 0.60 | — | 0.60 | 0.01 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.60 | 0.70 | 0.90 | 0.70 | 0.60 | 1.50 |
| Mannanase | 0.07 | 0.05 | 0.045 | 0.06 | 0.04 | 0.045 | 0.10 |
| Amylase 1 | 0.30 | — | 0.30 | 0.10 | — | 0.40 | 0.10 |
| Amylase 2 | — | 0.20 | 0.10 | 0.15 | 0.07 | — | 0.10 |
| Xyloglucanase | 0.20 | 0.10 | — | — | 0.05 | 0.05 | 0.20 |
| Lipase | 0.40 | 0.20 | 0.30 | 0.10 | 0.20 | — | — |
| Polishing enzyme | — | 0.04 | — | — | — | 0.004 | — |
| Nuclease | 0.05 | — | — | — | — | — | 0.003 |
| Dispersin B | — | — | — | 0.05 | 0.03 | 0.001 | 0.001 |
| Liquitint ® V200 | 0.01 | — | — | — | — | — | 0.005 |
| Leuco composition | 0.05 | 0.035 | 0.01 | 0.02 | 0.20 | 0.002 | 0.004 |
| Dye control agent | — | 0.3 | — | 0.03 | — | 0.3 | 0.3 |
| Water, dyes & minors | | | | Balance | | | |
| pH | | | | 8.2 | | | |

Based on total cleaning and/or treatment composition weight. Enzyme levels are reported as raw material.

Examples 8 to 18: Unit Dose Compositions

These examples provide various formulations for unit dose laundry care compositions. Compositions 8 to 12 comprise a single unit dose compartment. The film used to encapsulate the compositions is polyvinyl-alcohol-based film.

| Ingredients | 8 | 9 | 10 | 11 | 12 |
|---|---|---|---|---|---|
| | % weight of overall composition | | | | |
| LAS | 19.09 | 16.76 | 8.59 | 6.56 | 3.44 |
| AE3S | 1.91 | 0.74 | 0.18 | 0.46 | 0.07 |
| AE7 | 14.00 | 17.50 | 26.33 | 28.08 | 31.59 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI | 0.10 | — | 0.20 | — | — |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulfonate | — | — | — | — | 2.0 |
| Protease | 0.80 | 0.60 | 0.07 | 1.00 | 1.50 |
| Mannanase | 0.07 | 0.05 | 0.05 | 0.10 | 0.01 |
| Amylase 1 | 0.20 | 0.11 | 0.30 | 0.50 | 0.05 |
| Amylase 2 | 0.11 | 0.20 | 0.10 | — | 0.50 |
| Polishing enzyme | 0.005 | 0.05 | — | — | — |
| Nuclease | 0.- | 0.05 | — | — | 0.005 |
| Dispersin B | 0.010 | 0.05 | 0.005 | 0.005 | — |
| Cyclohexyl dimethanol | — | — | — | 2.0 | — |
| Leuco composition | 0.06 | 0.03 | 0.10 | 0.02 | 0.04 |
| Liquitint ® V200 | — | — | 0.01 | 0.05 | — |
| Structurant | 0.14 | 0.14 | 0.14 | 0.14 | 0.14 |
| Perfume | 1.9 | 1.9 | 1.9 | 1.9 | 1.9 |
| Dye control agent | 0.1 | 0.3 | 0.2 | 0.5 | 0.3 |
| Water and miscellaneous | To 100% | | | | |
| pH | 7.5-8.2 | | | | |

Based on total laundry care composition weight. Enzyme levels are reported as raw material.

In the following examples the unit dose has three compartments, but similar compositions can be made any number of compartments. The film used to encapsulate the compartments is polyvinyl alcohol.

| Ingredients | Base compositions | | | |
|---|---|---|---|---|
| | 13 | 14 | 15 | 16 |
| | % weight of overall composition | | | |
| HLAS | 26.82 | 16.35 | 7.50 | 3.34 |
| AE7 | 17.88 | 16.35 | 22.50 | 30.06 |
| Citric Acid | 0.5 | 0.7 | 0.6 | 0.5 |
| C12-15 Fatty acid | 16.4 | 6.0 | 11.0 | 13.0 |
| Polymer 1 | 2.9 | 0.1 | — | — |
| Polymer 3 | 1.1 | 5.1 | 2.5 | 4.2 |
| Cationic cellulose polymer | — | — | 0.3 | 0.5 |
| Polymer 6 | — | 1.5 | 0.3 | 0.2 |
| Chelant 2 | 1.1 | 2.0 | 0.6 | 1.5 |
| Optical Brightener 1 | 0.20 | 0.25 | 0.01 | 0.005 |
| Optical Brightener 3 | 0.18 | 0.09 | 0.30 | 0.005 |
| DTI | 0.1 | — | 0.05 | — |
| Glycerol | 5.3 | 5.0 | 5.0 | 4.2 |
| Monoethanolamine | 10.0 | 8.1 | 8.4 | 7.6 |
| Polyethylene glycol | — | — | 2.5 | 3.0 |
| Potassium sulfite | 0.2 | 0.3 | 0.5 | 0.7 |
| Protease | 0.80 | 0.60 | 0.40 | 0.80 |
| Amylase 1 | 0.20 | 0.20 | 0.200 | 0.30 |
| Polishing enzyme | — | — | 0.005 | 0.005 |
| Nuclease | 0.05 | — | — | — |
| Dispersin B | — | 0.010 | 0.010 | 0.010 |
| MgCl$_2$ | 0.2 | 0.2 | 0.1 | 0.3 |
| Structurant | 0.2 | 0.1 | 0.2 | 0.2 |
| Perfume/encapsulates | 0.10 | 0.30 | 0.01 | 0.05 |
| Dye control agent | 0.2 | 0.03 | 0.4 | — |
| Solvents and misc. | To 100% | | | |
| pH | 7.0-8.2 | | | |

| Ingredients | Finishing compositions | | | | | |
|---|---|---|---|---|---|---|
| | 17 | | | 18 | | |
| | Compartment | | | | | |
| | A | B | C | A | B | C |
| | Volume of each compartment | | | | | |
| | 40 ml | 5 ml | 5 ml | 40 ml | 5 ml | 5 ml |
| | Active material in Wt. % | | | | | |
| Perfume | 1.6 | 1.6 | 1.6 | 1.6 | 1.6 | 1.6 |
| Liquitint ® V200 | 0 | 0.006 | 0 | 0 | 0.004 | — |
| Leuco composition | — | 0.02 | — | — | 0.04 | — |
| TiO2 | — | — | 0.1 | — | — | 0.1 |
| Sodium Sulfite | 0.4 | 0.4 | 0.4 | 0.1 | 0.3 | 0.3 |
| Polymer 5 | — | — | — | 2 | — | — |
| Hydrogenated castor oil | 0.14 | 0.14 | 0.14 | 0.14 | 0.14 | 0.14 |
| Base Composition 13, 14, 15 or 16 | Add to 100% | | | | | |

Based on total laundry care composition weight, enzyme levels are reported as raw material.

| | |
|---|---|
| AE1.8S | is $C_{12-15}$ alkyl ethoxy (1.8) sulfate |
| AE3S | is $C_{12-15}$ alkyl ethoxy (3) sulfate |
| AE7 | is $C_{12-15}$ alcohol ethoxylate, with an average degree of ethoxylation of 7 |
| AE8 | is $C_{12-15}$ alcohol ethoxylate, with an average degree of ethoxylation of 8 |
| AE9 | is $C_{12-15}$ alcohol ethoxylate, with an average degree of ethoxylation of 9 |
| Amylase 1 | is Stainzyme ®, 15 mg active/g, supplied by Novozymes |
| Amylase 2 | is Natalase ®, 29 mg active/g, supplied by Novozymes |
| AS | is $C_{12-14}$ alkylsulfate |

| | |
|---|---|
| Xyloglucanase | is Whitezyme ®, 20 mg active/g, supplied by Novozymes |
| Chelant 1 | is diethylene triamine pentaacetic acid |
| Chelant 2 | is 1-hydroxyethane 1,1-diphosphonic acid |
| Dispersin B | is a glycoside hydrolase, reported as 1000 mg active/g |
| DTI | is either poly(4-vinylpyridine-1-oxide) (such as Chromabond S-403E ®), or poly(1-vinylpyrrolidone-co-1-vinylimidazole) (such as Sokalan HP56 ®). |
| Dye control agent | Dye control agent in accordance with the invention, for example Suparex ® O.IN (M1), Nylofixan ® P (M2), Nylofixan ® PM (M3), or Nylofixan ® HF (M4) |
| HSAS | is mid-branched alkyl sulfate as disclosed in U.S. Pat. No. 6,020,303 and U.S. Pat. No. 6,060,443 |
| LAS | is linear alkylbenzenesulfonate having an average aliphatic carbon chain length $C_9$-$C_{15}$ (HLAS is acid form). |
| Leuco composition | Any suitable leuco composition or mixtures thereof according to the instant disclosure. |
| Lipase | is Lipex ®, 18 mg active/g, supplied by Novozymes |
| Liquitint ® V200 | is a thiophene azo dye provided by Milliken |
| Mannanase | is Mannaway ®, 25 mg active/g, supplied by Novozymes |
| Nuclease | is a Phosphodiesterase SEQ ID NO 1, reported as 1000 mg active/g |
| Optical Brightener 1 | is disodium 4,4'-bis{[4-anilino-6-morpholino-s-triazin-2-yl]-amino}-2,2'-stilbenedisulfonate |
| Optical Brightener 2 | is disodium 4,4'-bis-(2-sulfostyryl)biphenyl (sodium salt) |
| Optical Brightener 3 | is Optiblanc SPL10 ® from 3V Sigma |
| Perfume encapsulate | is a core-shell melamine formaldehyde perfume microcapsules. |
| Polishing enzyme | is Para-nitrobenzyl esterase, reported as 1000 mg active/g |
| Polymer 1 | is bis(($C_2H_5O$)($C_2H_4O$)$n$)($CH_3$)—$N^+$—$C_xH_{2x}$—$N^+$—($CH_3$)-bis(($C_2H_5O$)($C_2H_4O$)$n$), wherein n = 20-30, x = 3 to 8 or sulphated or sulfonated variants thereof |
| Polymer 2 | is ethoxylated ($EO_{15}$) tetraethylene pentamine |
| Polymer 3 | is ethoxylated polyethylenimine |
| Polymer 4 | is ethoxylated hexamethylene diamine |
| Polymer 5 | is Acusol 305, provided by Rohm&Haas |
| Polymer 6 | is a polyethylene glycol polymer grafted with vinyl acetate side chains, provided by BASF. |
| Protease | is Purafect Prime ®, 40.6 mg active/g, supplied by DuPont |
| Structurant | is Hydrogenated Castor Oil |

Application Examples

I. Synthesis of Leuco Compositions

The following examples are provided to further illustrate the leuco compositions; however, they are not to be construed as limiting. While exemplary routes are disclosed for synthesizing the leuco compositions, the synthesis should not be limited to only these examples and synthetic routes. Additional starting materials and/or reagents for different synthetic routes and/or different leuco compositions that are not exemplified herein are also contemplated. In fact, it will be apparent to those skilled in the art that various modifications and variations can be made without departing from the scope or spirit of the disclosure. All parts and percentages given in these examples are by weight unless otherwise indicated.

Synthesis of Leuco Compositions:

Example leuco compositions 1-3, 5-7 and comparative example 8 were prepared following the general process below, described for compositions where the $Ar^1$ group is derived from $Ar^1$—C(O)H, but is readily adaptable.

A four-neck flask is equipped with an overhead stirrer, a condenser, a temperature controller, a heating mantle and a Nitrogen inlet. Then, about 2 moles of the coupler (normally giving rise to the radicals $Ar^2$ and $Ar^3$ in formula (I)) is added to the flask and heated to about 65-71° C. During heating, about 1 mole of $Ar^1$—C(O)H and catalytic amount (about 0.4 mole) urea pre-dissolved in small amount of water are added. After the above chemicals are mixed, about 1.2 mole of hydrochloric acid (in form of Muriatic acid) is added drop wise to control the temperature below 90-100° C. After the addition of hydrochloric acid, the reaction is stirred at 95-100° C. for about 7 hours.

Multiple methods can be used to retrieve the leuco colorant synthesized by the above process. One method is to neutralize the reaction product to pH about 9 and remove the water by rotary evaporation under reduced pressure. The resulting viscous material is diluted with an organic solvent such as isopropanol and filtered to remove the inorganic salts. The organic solvent is evaporated and the final product is obtained.

Example leuco composition 4 was prepared as herein described. In a 50 mL round bottom flask, 1.5 g (10.05 mmol) of p-dimethylaminobenzaldehyde and 2.77 g (21.12 mmol) of 1 methylindole is dissolved in 10 mL acetonitrile. To the solution, a few drop of methanesulfonic acid is added. The flask is then closed with a stopper and the reaction stirred with a magnetic stir bar and plate overnight at room temperature. The formed product precipitates out during this process and is collected by filtration. $^1$H-NMR confirms the structure and the purity of the material.

TABLE 1

Components used in preparing Leuco compositions 1-7 (example) and 8 (comparative).

| Example Leuco Composition | Compound[a] | Equiv.[c] | Compound[b] | Equiv.[c] |
|---|---|---|---|---|
| 1 | pyridine-2-carbaldehyde | 1 | 4-H-C6H4-N(CH2CH2O-C3H6OH)(CH2CH2O-(C3H6O)2H) | 2 |
| 2 | thiophene-2-carbaldehyde | 1 | 4-H-C6H4-N(CH2CH2O-C3H6OH)(CH2CH2O-(C3H6O)2H) | 2 |
| 3 | thiophene-2-carbaldehyde | 1 | 4-H-C6H4-N(CH2CH(O-)5H)(CH2CH(O-)5H) | 2 |
| 4 | 1-methylindole (3-H) | 2 | 4-(dimethylamino)benzaldehyde | 1 |
| 5 | 4-nitrobenzaldehyde | 1 | 4-H-C6H4-N(CH3)2 | 2 |
| 6 | furan-2-carbaldehyde | 1 | 3-methyl-4-H-C6H3-N(CH2CH(O-)10H)(CH2CH(O-)10H) | 2 |
| 7 | benzaldehyde | 1 | 4-H-C6H4-N(CH3)2 | 2 |

TABLE 1-continued

Components used in preparing Leuco compositions 1-7 (example) and 8 (comparative).

| Example Lueco Composition | Compound[a] | Equiv.[c] | Compound[b] | Equiv.[c] |
|---|---|---|---|---|
| 8 Comparative | 4-(dimethylamino)benzaldehyde structure | 1 | N,N-bis(2-hydroxyethyl)aniline structure | 2 |

[a] Represents $Ar^1$—C(O)H Examples 1-3, 5-7) or $Ar^2$—H and $Ar^3$—H (Example 4).
[b] Represents $Ar^2$—H and $Ar^3$—H (Examples 1-3, 5-7) or $Ar^3$—C(O)H (Example 4).
[c] Mole equivalents of the reactant used.

II. Stability of Laundry Care Compositions Comprising Leuco Compositions.

The following examples demonstrate the stability of leuco compositions as described in this disclosure. The leuco compositions as described in this disclosure resist changing from a colorless to a colored state under conditions that cause other leuco dyes to change to a colored state.

A nil-dye AATCC 2003 liquid reference detergent that contains no colorants or optical brightener was used to prepare seven different liquid detergent samples (samples 1-7), each containing one leuco composition as described in this disclosure. Sample 8 contained the leuco composition LCV-4EO as a positive control. The liquid detergent samples 1-7 contained 0.04 wt % leuco composition, and sample 8 contained 0.01 wt % leuco composition. The samples were prepared and stored in glass jars at 50° C. for 56 days. The visible absorbance spectrum of each detergent was measured on day 0 (the day the detergents were prepared), 7, 14, 28, and 56 days of storage. The change in absorbance over time at the $\lambda_{max}$ value for each leuco containing detergent sample ($\Delta\lambda_{max}=(\lambda_{max})_t-(\lambda_{max})_0$) was tracked over the course of sample storage, where t is the time in days and $(\lambda_{max})_0$ is the absorbance at the $\lambda_{max}$ for each detergent solution on the day of its preparation.

Leucomalachite green was purchased from Aldrich Chemical Company, St. Louis, Mo. Six additional leuco compositions were prepared according to the general methods disclosed herein. Structures for the samples are provided in Table 1 below. The $\lambda_{max}$ value of the colored state for each leuco composition was determined by taking an aliquot of each HDL sample, preparing a 1:10 dilution with deionized water, oxidizing to the corresponding triarylmethane dye with an ethanol solution of 2,3-dichloro-5,6-dicyano-p-benzoquinone, and measuring the visible absorbance spectrum of each dilution from 400-700 nm with a UV-Vis spectrophotometer.

The change in absorbance over time at the $\lambda_{max}$ value for leuco compositions 1-7 can be seen in Table 2 as compared to the change in absorbance of positive control sample 8. Samples 1-7 exhibited a very small changes in absorbance over time as compared to sample 8.

TABLE 2

Examples 1-8: Leuco compositions tested and $\Delta\lambda_{max}$ values at various storage times

| Example | Structure | $\lambda_{max}$ (nm) | $\Delta\lambda_{max}$ at t (days) | | | |
|---|---|---|---|---|---|---|
| | | | 7 | 14 | 28 | 56 |
| 1 | triarylmethane structure with pyridine and two N,N-bis((C$_3$H$_6$O)$_2$H ether) aniline groups | 648 | −0.0127 | −0.0158 | −0.0151 | −0.0036 |

TABLE 2-continued

Examples 1-8: Leuco compositions tested and Δλ$_{max}$ values at various storage times

| Example | Structure | Δ$_{max}$ (nm) | Δλ$_{max}$ at t (days) | | | |
|---|---|---|---|---|---|---|
| | | | 7 | 14 | 28 | 56 |
| 2 | [structure: bis(4-(N,N-bis(2-(C3H6O)2H-oxyethyl)amino)phenyl)(thiophen-2-yl)methane] | 634 | 0.0343 | 0.0351 | 0.0636 | 0.0939 |
| 3 | [structure: bis(4-(N,N-bis((CH2CH2O)5H)amino)phenyl)(thiophen-2-yl)methane] | 634 | 0.0173 | 0.0181 | 0.0356 | 0.0574 |
| 4 | [structure: (4-(dimethylamino)phenyl)bis(1-methyl-1H-indol-3-yl)methane] | 544 | 0.0129 | 0.0230 | 0.0355 | 0.0643 |

TABLE 2-continued

Examples 1-8: Leuco compositions tested and Δλ$_{max}$ values at various storage times

| Example | Structure | λ$_{max}$ (nm) | Δλ$_{max}$ at t (days) | | | |
|---|---|---|---|---|---|---|
| | | | 7 | 14 | 28 | 56 |
| 5 | [structure: bis(4-dimethylaminophenyl)(4-nitrophenyl)methane] | 652 | −0.0084 | 0.0013 | −0.0063 | −0.0041 |
| 6 | [structure: bis[3-methyl-4-(N,N-bis(decaethyleneglycol))aminophenyl](furan-2-yl)methane] | 648 | −0.0171 | −0.0248 | −0.0308 | −0.0381 |
| 7 | [structure: bis(4-dimethylaminophenyl)(phenyl)methane] | 626 | −0.0114 | −0.0088 | 0.0013 | 0.0167 |

TABLE 2-continued

Examples 1-8: Leuco compositions tested and $\Delta\lambda_{max}$ values at various storage times

| Example | Structure | $\lambda_{max}$ (nm) | $\Delta\lambda_{max}$ at t (days) | | | |
|---|---|---|---|---|---|---|
| | | | 7 | 14 | 28 | 56 |
| 8 (Comparative Example) | [structure: tris(4-aminophenyl)methane derivative with bis(2-hydroxyethyl)amino groups on two phenyl rings and a dimethylamino group on the third] | 597 | 0.0847 | 0.1508 | 0.1686 | 0.4238 |

III. Authentication Test for a Laundry Care Composition

A change from a first color to a second color in the laundry care composition of the present disclosure is detected using both visual and spectrophotometric methods. In this example, the authentication test comprises the following general procedure for each formulation tested.
(1) Prepare a 1:5 dilution by mixing 20.0 mL of the laundry care composition with 80.0 mL of deionized water.
(2) Measure the first color of the diluted formulation from step (1) above by the spectrophotometric method disclosed herein.
(3) Add the triggering agent (0.200 mL of a solution that is 0.031 M N-Bromosuccinimide in ethanol) to 50.0 mL of the diluted formulation from step (1) above and shake the resulting solution for 1 minute.
(4) Make a visual assessment to determine if the difference between the first color and the second color of the diluted formulation is easily discerned.
(5) Measure the second color of the diluted, triggered formulation from step (3) above by the spectrophotometric method disclosed herein.
(6) Calculate the color change score (DE*) for the change in appearance between the first color and the second color.

The authentication test was performed on laundry care formulations A1 and C1, each prepared from AATCC Standard Reference (HE) Liquid Detergent WOB (obtained from AATCC June 2017) that contains no colorants or optical brightener. Formulation A1 comprises 0.04 wt % of a leuco composition according to the present invention and represents an authentic product. Formulation C1 is absent any leuco composition and represents a counterfeit product. The results are indicated in the Table below.

TABLE 3

Results of Authentication Test for Laundry Care Compositions

| Formulation | Assessment of Color Change | |
|---|---|---|
| | Visual observation | Spectrophotometric (DE* Color Score) |
| A1 | Color change discerned | 11.74 |
| C1 | No change | 0.10 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of detecting an authentic composition, the method comprising the steps of:
   a) providing a composition having a first color, wherein the composition is selected from the group consisting of perfume compositions, fuel compositions, lubricant compositions, thermoplastic polymer compositions, polyol compositions, polyurethane compositions, and seed coating compositions, and wherein the composition comprises at least one leuco compound of Formula (III) or Formula (IV):

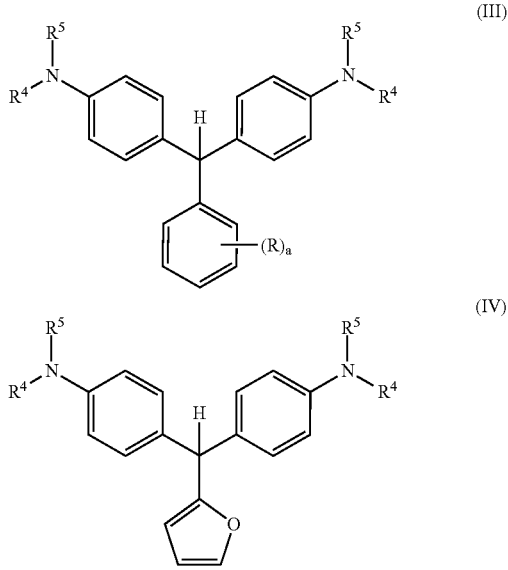

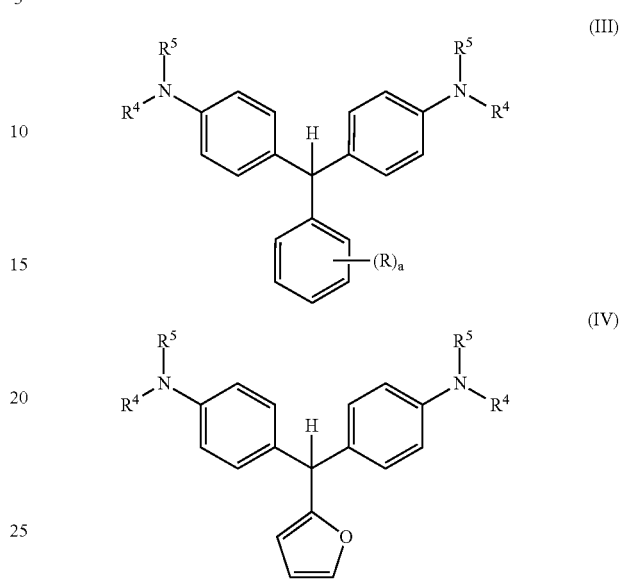

wherein each R is an electron withdrawing substituent independently selected from the group consisting of trihalides, cyano, sulfonates, sulfonate esters, sulfones, sulfoxides, ammonium, quaternary amines, nitro, aldehydes, ketones, carboxylic acid, carboxylic acid esters, acyl chloride, amides, and halides, and wherein each $R^4$ and $R^5$ is independently selected from the group consisting of: H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, and polyoxyalkylene;

b) adding a triggering agent to the composition, wherein the triggering agent is selected from the group consisting of sodium hypochlorite, calcium hypochlorite, sodium dichlorocyanurate, alkali metal N-chloro(4-methylbenzene)sulfonamide, N-chlorosulfamate, N-bromosuccinimide, tetrachloro-1,2-benzoquinone, 2,3-dichloro-5,6-dicyano-p-benzoquinone, and mixtures thereof, and wherein the triggering agent causes the at least one leuco compound to change from a colorless state to a colored state; and c) detecting the change, wherein the change from the first color to the second color is visually perceptible.

2. The method of claim 1, wherein the change from the first color to the second color has a color change score (DE*) of at least 2.

3. The method of claim 1, wherein the leuco compound is a compound of Formula (IV).

4. A test kit for detecting authentic compositions comprising:

a. a receptacle for receiving an amount of a composition selected from the group consisting of perfume compositions, fuel compositions, lubricant compositions, thermoplastic polymer compositions, polyol compositions, polyurethane compositions, and seed coating compositions;

b. a triggering agent selected from the group consisting of sodium hypochlorite, calcium hypochlorite, sodium dichlorocyanurate, alkali metal N-chloro(4-methylbenzene)sulfonamide, N-chlorosulfamate, N-bromosuccinimide, tetrachloro-1,2-benzoquinone, 2,3-dichloro-5,6-dicyano-p-benzoquinone, and mixtures thereof, wherein the triggering agent converts a leuco compound of Formula (III) or Formula (IV):

in a composition from a colorless to a colored state, wherein each R is an electron withdrawing substituent independently selected from the group consisting of trihalides, cyano, sulfonates, sulfonate esters, sulfones, sulfoxides, ammonium, quaternary amines, nitro, aldehydes, ketones, carboxylic acid, carboxylic acid esters, acyl chloride, amides, and halides, and wherein each $R^4$ and $R^5$ is independently selected from the group consisting of: H, $C_{1-16}$ branched alkyl, $C_{1-16}$ linear alkyl, $C_{1-16}$ substituted branched alkyl, $C_{1-16}$ substituted linear alkyl, $C_{7-16}$ substituted alkaryl, $C_{7-16}$ unsubstituted alkaryl, and polyoxyalkylene; and c. instructions for combining the composition and triggering agent to detect authentic compositions.

5. The test kit of claim 4, wherein the instructions comprise a color index.

6. The method of claim 1, wherein at least one $R^4$ and $R^5$ is a polyoxyalkylene comprising 3 to 60 ethylene oxide repeating units.

7. The method of claim 6, wherein $R^4$ and $R^5$ are polyoxyalkylenes comprising 3 to 60 ethylene oxide repeating units.

8. The method of claim 7, wherein $R^4$ and $R^5$ are polyoxyalkylenes comprising 10 to 25 ethylene oxide repeating units.

9. The test kit of claim 4, wherein the leuco compound is a compound of Formula (IV).

10. The test kit of claim 4, wherein at least one $R^4$ and $R^5$ is a polyoxyalkylene comprising 3 to 60 ethylene oxide repeating units.

11. The test kit of claim 10, wherein $R^4$ and $R^5$ are polyoxyalkylenes comprising 3 to 60 ethylene oxide repeating units.

12. The test kit of claim 11, wherein $R^4$ and $R^5$ are polyoxyalkylenes comprising 10 to 25 ethylene oxide repeating units.

\* \* \* \* \*